(12) United States Patent
Metzger et al.

(10) Patent No.: US 6,774,230 B2
(45) Date of Patent: Aug. 10, 2004

(54) METHODS FOR THE PREPARATION OF MIRTAZAPINE INTERMEDIATES

(75) Inventors: Leonid Metzger, Beersheba (IL); Shlomit Wizel, Petah Tiqva (IL)

(73) Assignee: Teva Pharmaceutical Industries, Ltd., Petah Tiqva (IL)

( * ) Notice: Subject to any disclaimer, the term of this patent is extended or adjusted under 35 U.S.C. 154(b) by 0 days.

(21) Appl. No.: 10/073,960

(22) Filed: Feb. 14, 2002

(65) Prior Publication Data

US 2002/0165238 A1 Nov. 7, 2002

Related U.S. Application Data

(60) Provisional application No. 60/272,699, filed on Mar. 1, 2001.

(51) Int. Cl.$^7$ .................... C07D 401/04; C07D 471/14
(52) U.S. Cl. ........................................ 540/578; 544/365
(58) Field of Search .......................... 544/365; 540/578

(56) References Cited

U.S. PATENT DOCUMENTS

| 4,062,848 | A | 12/1977 | van der Burg |
| 6,376,668 | B1 | 4/2002 | Iishi et al. ................. 544/360 |

*Primary Examiner*—Emily Bernhardt
(74) *Attorney, Agent, or Firm*—Kenyon & Kenyon

(57) ABSTRACT

The preparation of 1-(3-carboxypyridyl-2)-4-methyl-2-phenylpiperazine dihydrate and other mirtazapine intermediates are described. These compounds are particularly useful in the preparation of mirtazapine.

13 Claims, 2 Drawing Sheets

METHODS FOR THE PREPARATION OF MIRTAZAPINE INTERMEDIATES

CROSS-REFERENCE TO RELATED APPLICATION

This application claims the benefit of U.S. Provisional Application No. 60/272,699, filed on Mar. 1, 2001.

FIELD OF THE INVENTION

The invention relates to the preparation of certain piperazine ring-containing compounds. More particularly, the invention relates to 1-(3-carboxypyridyl-2)-4-methyl-2-phenylpiperazine dihydrate, methods for its preparation, and methods for its use in the preparation of mirtazapine.

BACKGROUND OF THE INVENTION

Mirtazapine, 1,2,3,4,10,14b-hexahydro-2-methylpyrazino [2,1-a] pyrido [2,3-c][2]benzazepine, is the first agent in a new class of antidepressant compounds called piperazinoazepine-derivatives. Mirtazapine is the active ingredient in REMERON, manufactured by Organon, and is approved by the United States Food and Drug Administration for the treatment of depression. Conventional therapeutics for treating depression include selective serotonin reuptake inhibitors (e.g., fluoxetine), monoamine oxidase inhibitors (e.g. phenelzine), and tricyclic antidepressant agents (e.g. doxepin).

Evidence suggests that mirtazapine acts as an antagonist at central presynaptic $\alpha_2$-adrenergic autoreceptors and heteroreceptors, thereby possibly resulting in increased central noradrenergic and serotonergic neurotransmission. Mirtazapine is a potent antagonist of serotonin type 2 (5-HT$_2$) and type 3 (5-HT$_3$) receptors, but the drug does not exhibit any significant affinity for serotonin type 1A (5-HT$_{1A}$) or type 1B (5-HT$_{1B}$) receptors. Mirtazapine is a potent antagonist of histamine (H$_1$) receptors, is a moderate antagonist at muscarinic receptors, and exhibits moderate peripheral $\alpha_2$-adrenergic blocking activity. Because of its unique pharmacodynamic properties, mirtazapine is an effective, safe and well-tolerated antidepressant agent that has demonstrated important anxiolytic and sleep-improving effects.

As a tetracyclic agent, mirtazapine differs structurally from conventional therapeutics. Mirtazapine has the following chemical structure I:

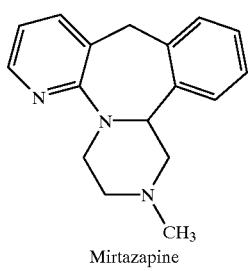

Mirtazapine

Mirtazapine can be prepared as shown in scheme 1, below.

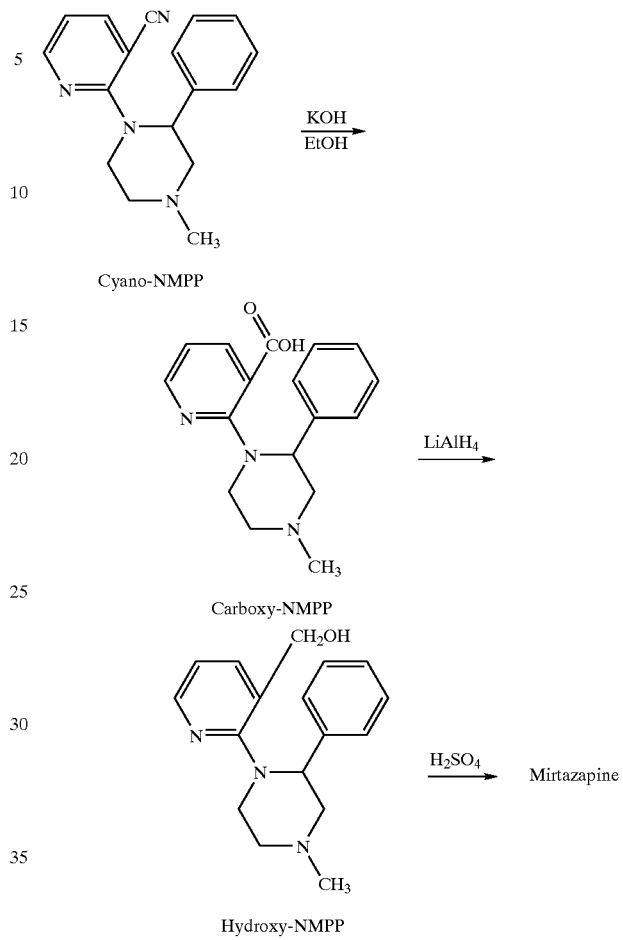

Scheme 1

Example 1 of U.S. Pat. No. 4,062,848 ("the '848 patent") describes a conventional manner for sequentially preparing each of the four compounds shown in scheme 1. For example, 1-(3-cyanopyridyl-2)-4-methyl-2-phenylpiperazine ("cyano-NMPP") is converted into the 1-(3-carboxypyridyl-2)-4-methyl-2-phenylpiperazine intermediate ("carboxy-NMPP") by the hydrolysis of the nitrile under highly basic conditions (potassium hydroxide) at high temperatures (100° C.) for a long time (24 h).

A need remains, however, for methods for preparing carboxy-NMPP dihydrate and other mirtazapine intermediates, which are useful, for example, in preparing mirtazapine.

SUMMARY OF THE INVENTION

Figure 1:
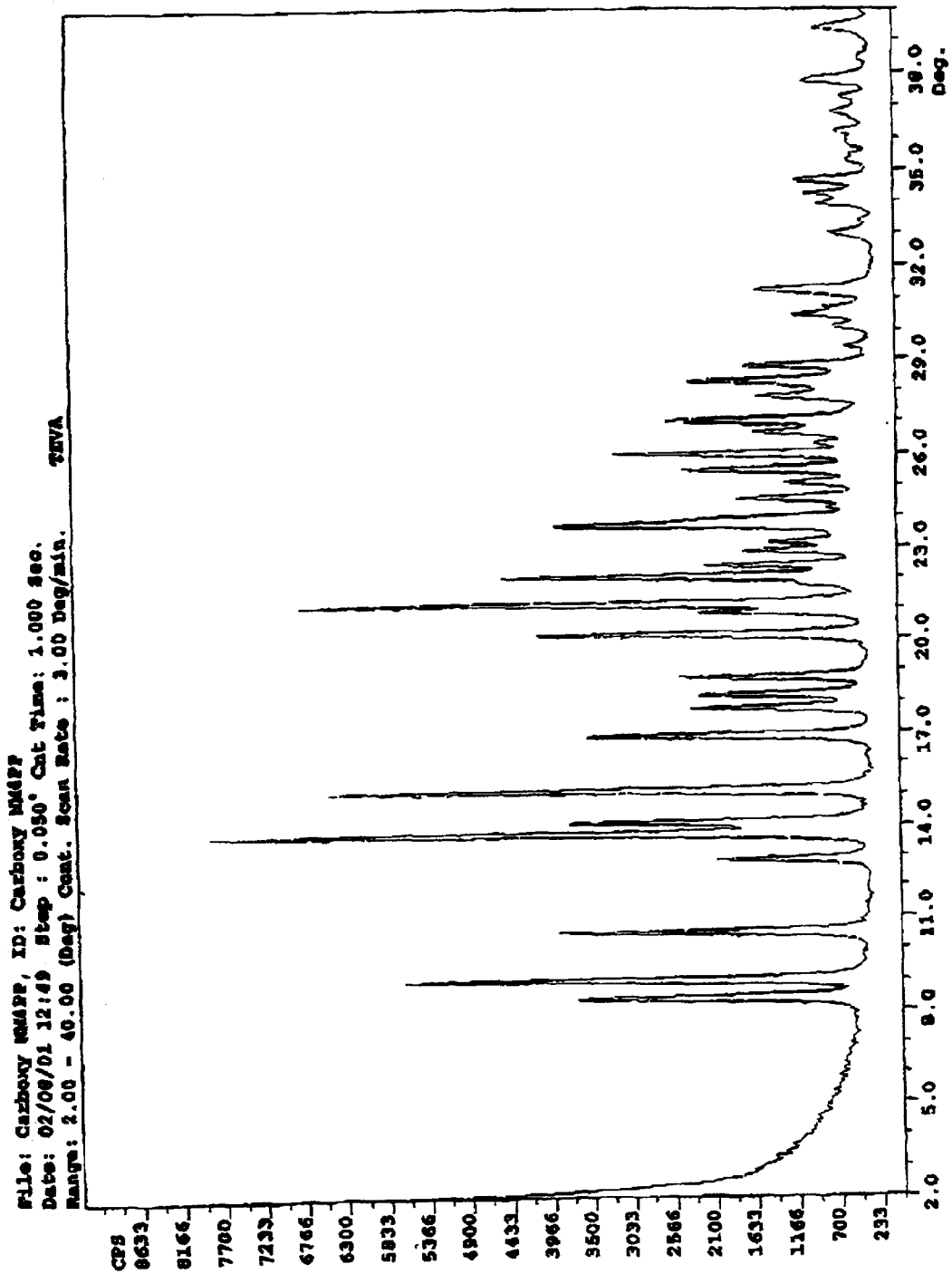
FIG. 1: X-Ray Diffraction Analysis of the carboxy-NMPP dihydrate obtained in Example 2.
Figure 2:
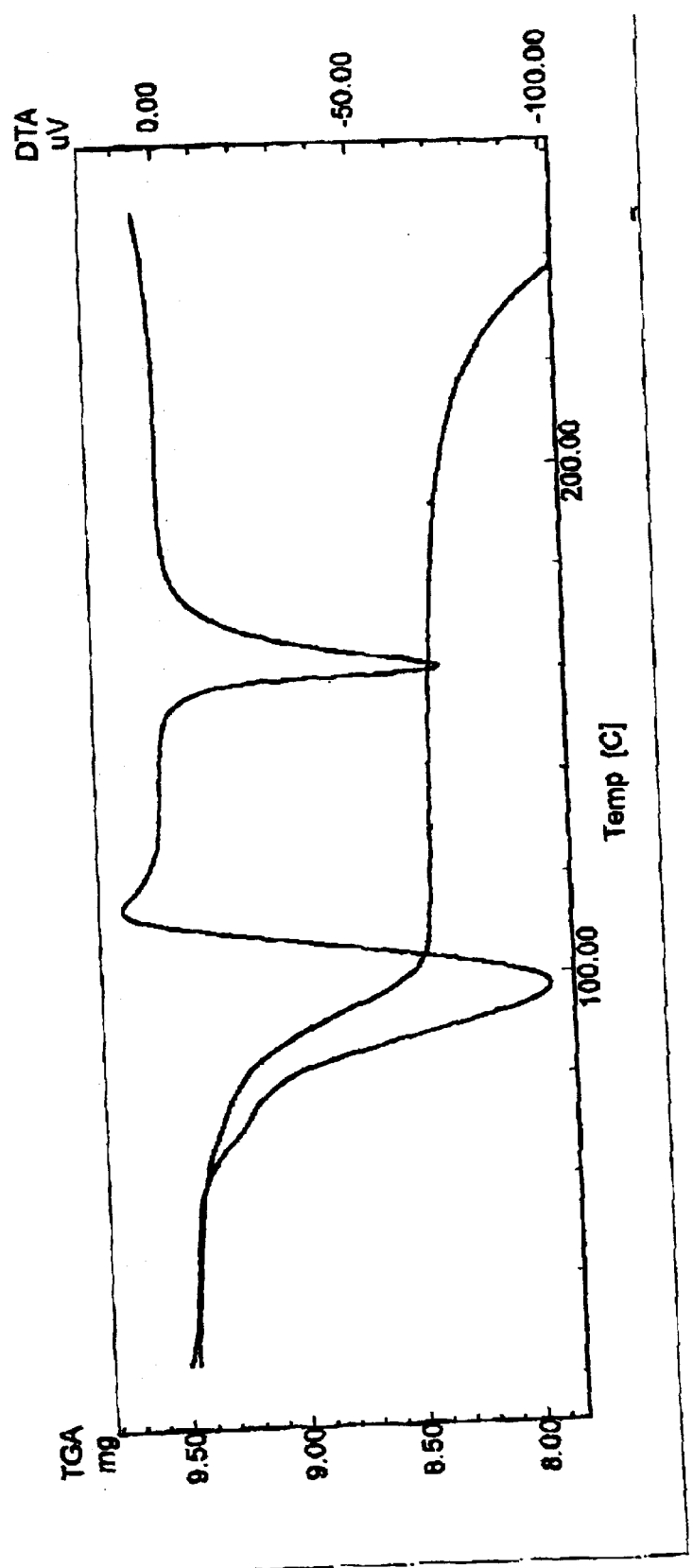
FIG. 2: Differential Thermal Gravimetry of the carboxy-NMPP dihydrate obtained in Example 2.

In one embodiment, the invention provides a novel dihydrate of carboxy-NMPP, which has been characterized by PXRD and Differential Thermal Gravimetry.

The invention also provides a novel process for the preparation of carboxy-NMPP dihydrate comprising heating a mixture of an aqueous solution of a 1-(3-carboxypyridyl- 2)-4-methyl-2-phenylpiperazine salt and an organic liquid; neutralizing the aqueous solution with an acid; and recovering 1-(3-carboxypyridyl-2)-4-methyl-2-phenylpiperazine dihydrate from the aqueous solution.

Another aspect of the invention provides a process for converting 1-(3-carboxypyridyl-2)-4-methyl-2-phenylpiperazine dihydrate to mirtazapine.

DETAILED DESCRIPTION OF THE INVENTION

Preparation of Carboxy-NMPP

Carboxy-NMPP can be prepared by various ways known in the art. One such process is described in Example I of the '848 patent, which is incorporated herein by reference. Alternatively, carboxy-NMPP can be prepared according to Example 1, below.

Preparation of Carboxy-NMPP Dihydrate

According to one embodiment of the invention, carboxy-NMPP dihydrate is prepared by heating a mixture of a basic salt solution of a carboxy-NMPP with one or more organic liquids; neutralizing the solution with an acid; and recovering the carboxy-NMPP dihydrate from the solution.

The basic salt solution can be any suitable strong inorganic or organic base. Examples include potassium hydroxide, sodium hydroxide, lithium hydroxide, barium hydroxide, and tetraalkylammonium hydroxide. Preferably, the basic salt solution comprises sodium hydroxide, or more preferably, potassium hydroxide.

Suitable organic liquids include, but are not limited to, methyl iso-butyl ketone, toluene, heptane, and mixtures thereof. Methyl iso-butyl ketone is preferred.

The heating step preferably continues until the reaction forming the dihydrate is complete. Refluxing for about half an hour, for example, is typical. The aqueous solution is then preferably separated from the one or more organic liquids before neutralization.

Neutralization is preferably achieved with an aqueous acid solution. Suitable acids include, but are not limited to, phosphoric acid, nitric acid, sulfuric acid, acetic acid, and, preferably, hydrochloric acid. The concentration of aqueous acid solution is preferably about 5-36% w/w. The neutralization step causes the carboxy-NMPP dihydrate to precipitate. Carboxy-NMPP dihydrate can then be recovered using methods known in the art, such as filtration.

Carboxy-NMPP dihydrate has the following structure:

II

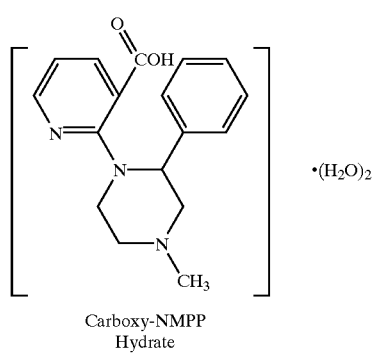

Carboxy-NMPP Hydrate

Preparation of Mirtazapine

Once carboxy-NMPP dihydrate is obtained, mirtazapine can then be prepared by reducing the carboxy-NMPP dihydrate and dehydrating the product therefrom. Methods for reducing and dehydrating similar compounds are well known in the art.

Examples of the invention are given below by way of illustration and not by way of limitation.

EXAMPLES

Example 1

Preparation of Carboxy-NMPP

Cyano-NMPP (40.0 g), dimethyl sulfoxide (2.0 g), KOH flakes (125.0 g) and tap water (62.5 ml) was charged into 500 ml 3-necked round bottomed flask equipped with gas tube, mechanical stirrer and water condenser. The reaction mixture was heated to about 150° C. with stirring in atmosphere of nitrogen for about 7 hours and then the reaction was cooled to about 110° C.

Toluene (145 g) was added and the mixture was stirred for about 30 minutes at about 100° C. The mixture was transferred into a heated separation funnel, kept at a constant temperature for about 15 to 20 minutes without stirring and was then separated.

The aqueous (lower) phase was transferred into 500 ml 3-necked round bottomed flask equipped with mechanical stirrer and dropping funnel and distillation system. Aqueous HCl (54.5 g) solution was added to obtain pH 7. Toluene (508 g) was added to the reaction mixture. The mixture was heated to reflux and then azeotropic distillation was performed at about 86 to 110° C. The mixture was cooled to about 25° C. and formed salts was filtered with suction to get clear filtrate, which was washed with about boiling toluene (80 g), cooled and filtered again. The clear filtrate was charged into 1 L round bottomed flask and evaporated under reduced pressure to dryness to give carboxy-NMPP.

Example 2

Preparation of Carboxy-NMPP Dihydrate

The flask containing dry carboxy-NMPP prepared in Example 1 was connected to a V-adapter mechanical stirrer and 100 ml dropping funnel. Aqueous KOH (90 g) solution was charged into the dropping funnel and added dropwise with stirring at room temperature to give brown clear carboxy-NMPP potassium salt aqueous solution with pH 14.

Methyl iso-butyl ketone (108 ml) was added to the aqueous phase and the mixture was refluxed for about 30 minutes.

The mixture was cooled to room temperature and then transferred into a 500 ml separation funnel. The aqueous layer, containing carboxy-NMPP potassium salt, was separated.

The base excess was then neutralized with aqueous HCl (29.6 g) solution to give a mixture with pH 7. Some yellowish precipitation occurred in the aqueous solution. The precipitate was filtered with suction and washed with water (20 ml). The product was dried on air with suction at room temperature. The overall yield of dry carboxy-NMPP hydrate was 10.5 g (23%).

The carboxy-NMPP dihydrate was characterized by PXRD peaks: 8.4, 9.0, 10.5, 12.9, 13.7, 14.1, 15.1, 16.7, 17.8, 18.2, 18.8, 20.1, 20.9, 21.2, 22.0, 22.4, 22.9, 23.2, 23.7, 24.6, 25.1, 25.5, 26.0, 26.7, 27.0, 27.8, 28.3, 28.8, 29.4, 30.1, 31.2, 33.0, 34.2, 34.7, 36.2, 36.8, 37.8, 39.4±0.2 degrees two theta.

A Scintag x-ray powder diffractometer was used having a variable goniometer, Cu-tube, solid state detector, and equipped with a 12 round positions autosampler. The sample holder was a round standard aluminum sample holder with round zero background quartz plate. The scanning range was 2θ=2° to 40° continuous scan, with a scan rate of 3 deg/min.

Differential Thermal Gravimetry of carboxy-NMPP dihydrate showed an endothermic peak at 97° C. due to water release. This endotherm was followed by an exothermic peak at 114° C. The weight loss between 97° C. and 114° C. is 10.95%. This value is in agreement with Karl-Fischer water analysis of 10.74% for carboxy-NMPP dihydrate. A second endothermic peak was observed at 160° C. These determinations were made with using a Shimadev DTG-50 with the following experimental parameters: a temperature range of up to 250° C. and a heating rate of 10° C./h.

The carboxy-NMPP dihydrate contained about 10.7±1.0 weight percent water.

What is claimed is:

1. 1-(3-carboxypyridyl-2)-4-methyl-2-phenylpiperazine dihydrate.

2. A process for preparing 1-(3-carboxypyridyl-2)-4-methyl-2-phenylpiperazine dihydrate comprising the steps of:

heating a mixture of a basic salt solution of a 1-(3-carboxypyridyl-2)-4-methyl-2-phenylpiperazine and an organic solvent; and allowing 1-(3-carboxypyridyl-2)-4-methyl-2-phenylpiperazine dihydrate to form.

3. The process of claim 2, further comprising: recovering 1-(3-carboxypyridyl-2)-4-methyl-2-phenylpiperazine dihydrate from the solution.

4. The process of claim 2, wherein the basic salt solution comprises a base selected from the group consisting of potassium hydroxide, sodium hydroxide, lithium hydroxide, barium hydroxide, and tetraalkylammonium hydroxide.

5. The process of claim 4, wherein the basic salt solution comprises potassium hydroxide.

6. The process of claim 2, wherein the organic solvent is selected from the group consisting of methyl iso-butyl ketone, toluene, heptane, and mixtures thereof.

7. The process of claim 6, wherein the organic solvent is selected from the group consisting of (a) methyl iso-butyl ketone and (b) mixtures of methyl iso-butyl ketone and (i) toluene (ii) heptane or (iii) toluene and heptane.

8. The process of claim 2, wherein the heating step comprises refluxing.

9. The process of claim 2, further comprising neutralizing the solution with an acid.

10. The process of claim 9, wherein the acid is an aqueous acid solution.

11. The process of claim 10, wherein the aqueous acid solution comprises an acid selected from the group consisting of phosphoric acid, nitric acid, sulfuric acid, acetic acid and hydrochloric acid.

12. The process of claim 10, wherein the aqueous acid solution comprises about 5–36% w/w hydrochloric acid.

13. A process for preparing mirtazapine comprising converting 1-(3-carboxypyridyl-2)-4-methyl-2-phenylpiperazine dihydrate to mirtazapine, wherein the converting step comprise:

reducing carboxy-NMPP dihydrate to form hydroxy-NMPP; and dehydrating the hydroxy-NMPP to form mirtazapine.

* * * * *